US00PP11451P

United States Patent [19]

Bartels

[11] Patent Number: Plant 11,451

[45] Date of Patent: Jul. 18, 2000

[54] ASTER PLANT NAMED 'DASFOUR'

[75] Inventor: Goos B. H. Bartels, Aalsmeer, Netherlands

[73] Assignee: Bartels Stek, Aalsmeer, Netherlands

[21] Appl. No.: 09/145,841

[22] Filed: Sep. 3, 1998

[51] Int. Cl.[7] ..... A01H 5/00

[52] U.S. Cl. ..... Plt./355

[58] Field of Search ..... Plt./355

[56] References Cited

U.S. PATENT DOCUMENTS

P.P. 10,359 4/1998 Kristiansen ..... Plt./355

P.P. 10,360 4/1998 Kristiansen ..... Plt./355

P.P. 10,361 4/1998 Kristiansen ..... Plt./355

*Primary Examiner*—Howard J. Locker

*Assistant Examiner*—Michelle Kizilkaya

*Attorney, Agent, or Firm*—C. A. Whealy

[57] ABSTRACT

A distinct cultivar of potted Aster plant named 'Dasfour', characterized by its compact and uniform habit; freely and uniform flowering; daisy-type inflorescences with purple ray florets and yellow disc florets; tolerance to Powdery Mildew; and good post-production longevity.

1 Drawing Sheet

BACKGROUND OF THE INVENTION

The present invention relates to a new and distinct cultivar of potted Aster plant, botanically known as *Aster novi-belgii* and referred to by the cultivar name Dasfour.

The new Aster is a product of a planned breeding program conducted by the Inventor in Aalsmeer, The Netherlands. The objective of the breeding program was to create new compact potted Asters having desirable floret colors, uniform plant habit, and uniform flowering.

The new Aster originated from a cross made in 1992 by the Inventor of two proprietary Aster seedling selections. The cultivar Dasfour was discovered and selected by the Inventor as a flowering plant within the progeny of the stated cross in a controlled environment in Aalsmeer, The Netherlands. The new Aster differs from the parent selections in ray floret color and is more compact and more freely flowering.

Asexual reproduction of the new Aster by terminal cuttings taken at Aalsmeer, The Netherlands, has shown that the unique features of this new Aster are stable and reproduced true to type in succesive generations of asexual reproduction.

SUMMARY OF THE INVENTION

The following traits have been repeatedly observed and are determined to be the unique characteristics of 'Dasfour'. These characteristics in combination distinguish 'Dasfour' as a new and distinct cultivar:

1. Compact and uniform habit, excellent for pot plant culture.

2. Freely and uniform flowering.

3. Daisy-type inflorescences with purple ray florets and yellow disc florets. Ray floret color does not fade.

4. Tolerant to Powdery Mildew.

5. Good post-production longevity.

The cultivar Dasfour has not been observed under all possible environmental conditions. The phenotype may vary somewhat with variations in environment such as temperature, daylength and light intensity, without, however, any variance in genotype.

BRIEF DESCRIPTION OF THE PHOTOGRAPH

The accompanying colored photograph illustrates the overall appearance of the new Aster, showing the colors as true as it is reasonably possible to obtain in colored reproductions of this type. Colors in the photograph may differ slightly from the color values cited in the detailed botanical description which more accurately describe the actual colors of the new Aster. The photograph comprises a top perspective view of typical flowering plant of the new Aster. Ray floret and leaf colors in this photograph may appear different than the actual colors due to light reflectance.

DETAILED BOTANICAL DESCRIPTION

In this following description, color references are made to The Royal Horticultural Society Colour Chart except where general terms of ordinary dictionary significance are used. The following observations and measurements describe plants grown in Aalsmeer, The Netherlands, in a glass-covered greenhouse with average day and night temperatures of 19 and 17° C., respectively. Plants received long day/short night treatments for the first seven weeks, then short day/long night treatments for the next five weeks. Plants were pinched (terminal apices removed) two weeks after planting.

Botanical classification: *Aster novi-belgii* cultivar Dasfour.

Commercial classification: Potted Aster.

Parentage:

*Male or pollen parent.*—Proprietary *Aster novi-belgii* seedling selection.

*Female or seed parent.*—Proprietary *Aster novi-belgii* seedling selection.

Propagation:

*Type.*—Terminal tip cuttings.

*Time to rooting.*—Summer: About 28 days at a temperature of 20° C. Winter: About 35 days at a temperature of 18° C.

*Rooting habit.*—Fine, fibrous and well-branched.

Plant description:

*Appearance.*—Perennial herbaceous decorative container plant. Compact with flattened to slightly mounded plant plane; stems upright to outward forming an inverted triangle. appropriate for 10 to 14-cm containers. Usually about 12 weeks are required to produce a flowering plant.

*Branching habit.*—Freely branching; pinching enhances branching; typically four lateral branches develop after pinching.

*Growth rate.*—Relatively slow.

*Plant height.*—About 25 cm.

*Plant width.*—About 25 cm.

*Lateral branch length.*—About 20 cm.

*Internode length.*—About 1 cm.

*Stem color.*—147A with slight anthocyanin.

*Foliage description.*—Arrangement: Alternate. Shape: Roughly ovate, narrow; Apex acute; base attenuate; margin slightly serrated. Length, largest leaves: About 10 cm. Width, largest leaves: About 1 cm. Texture: Glabrous, leathery. Color: Young leaves, upper surface: 137A. Young leaves, lower surface: 137B. Fully expanded leaves, upper surface: 147A. Fully expanded leaves, lower surface: 147B. Venation, upper surface: 147B. Venation, lower surface: 147B.

Flowering description:

*Appearance.*—Daisy inflorescence form. Flattened inflorescences borne on terminals above foliage, arising from leaf axils; inflorescences face upright. Disc and ray florets arranged acropetally on a capitulum.

*Flowering response.*—Under natural conditions, plants flower in the late summer/autumn. At other times of the year, inflorescence initiation and development can be induced under short day/long night conditions. Response time is about 12 weeks.

*Post-production longevity.*—Good, inflorescences last about four weeks on the plant. Inflorescences persistent.

*Quantity of Inflorescences.*—Inflorescences form at every leaf axil. Freely, flowering, usually about 55 inflorescences per plant.

*Inflorescence size.*—Diameter: About 2.5 cm. Depth (height): About 1 cm.

*Bud.*—Shape: Ovoid. Length: About 1.5 cm. Diameter: About 5 mm.

*Ray florets.*—Number of rows of ray florets per inflorescence: Usually two. Shape: Oblong; apex acute; base attenuate; margin entire. Length: About 1 cm. Width: About 3 mm. Texture: Satiny, smooth and glabrous. Color: When opening, upper surface: 77A to 77B. When opening, lower surface: 83D. Mature, upper surface: 77B, color does not fade. Mature, lower surface: 83D.

*Disc florets.*—Quantity: About 40 per inflorescence. Shape: Tubular; apex dentate. Length: About 1 mm. Width: About 2 mm. Color: Immature: 7A. Mature: 9B.

*Sepals.*—Appearance: Leaf-like. Quantity: Several rows. Shape: Linear; apex sharply pointed; margin entire. Texture: Slightly pubescent. Color: Upper surface: 137A. Lower surface: 147B.

*Peduncle.*—Aspect: Angled about 45° to the stem. Strength: Strong. Length: Apical peduncle: About 1 cm. Fourth peducle: About 7 cm. Seventh peduncle: About 6 cm. Texture: Glabrous. Color: 137A.

*Reproductive organs.*—Androecium: Present on disc florets only. Pollen: Moderate, 9B in color. Gynoecium: Present on both ray and disc florets.

Disease resistance: Tolerant to Powdery Mildew.

Seed production: Seed production has not been observed.

It is claimed:

1. A new and distinct cultivar of Aster plant named 'Dasfour', as illustrated and described.

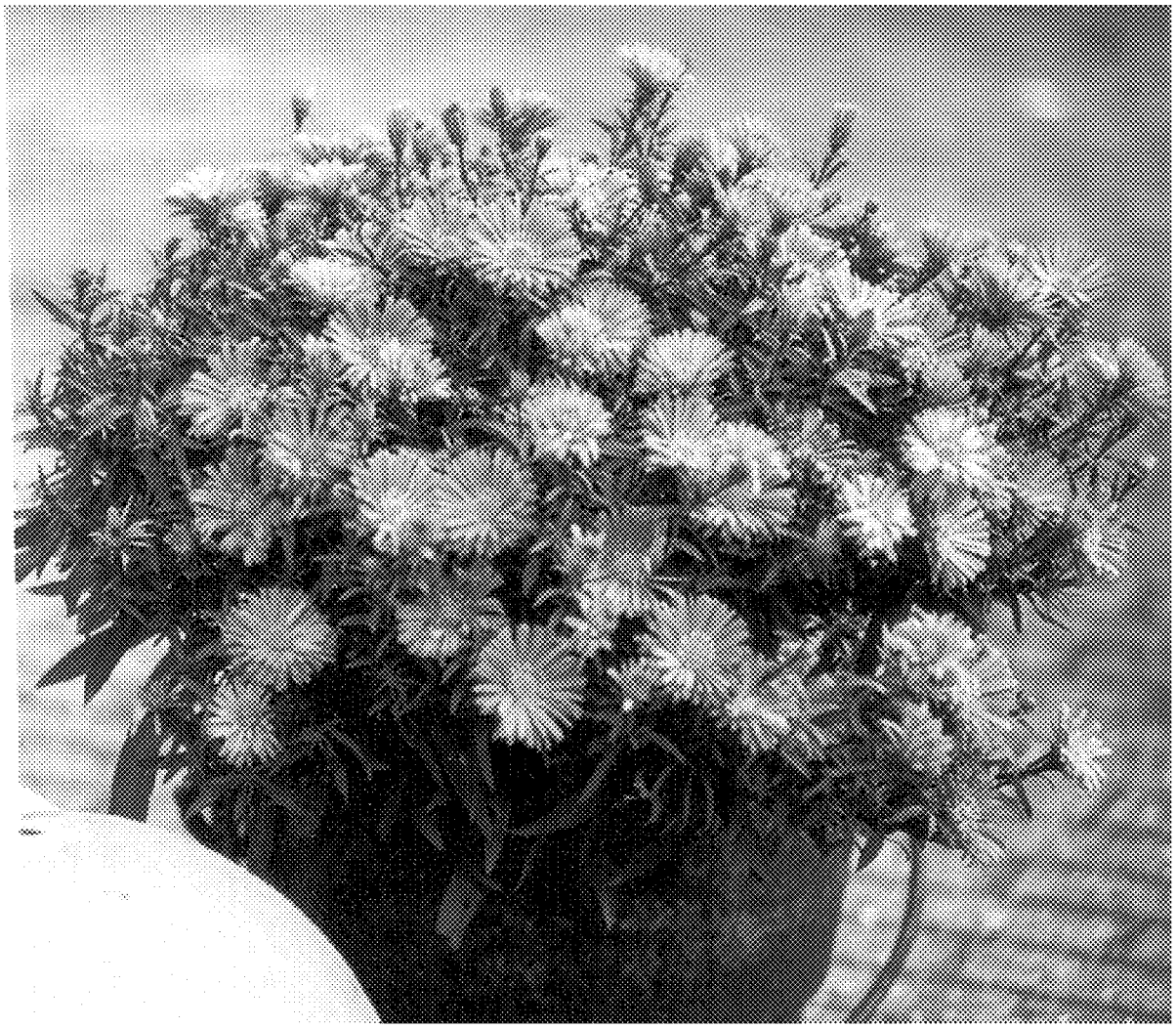

* * * * *